(12) United States Patent
Saguchi et al.

(10) Patent No.: US 7,399,501 B2
(45) Date of Patent: Jul. 15, 2008

(54) GAS SENSOR MANUFACTURING PROCESS

(75) Inventors: Takashi Saguchi, Kani (JP); Hiroshi Matsuzaki, Iwakura (JP)

(73) Assignee: NGK Spark Plug Co., Ltd., Aichi (JP)

( * ) Notice: Subject to any disclaimer, the term of this patent is extended or adjusted under 35 U.S.C. 154(b) by 840 days.

(21) Appl. No.: 10/701,554

(22) Filed: Nov. 6, 2003

(65) Prior Publication Data
US 2004/0140212 A1   Jul. 22, 2004

(30) Foreign Application Priority Data
Nov. 6, 2002  (JP)  .......................... P.2002-322627

(51) Int. Cl.
C23C 14/34 (2006.01)
C23C 16/00 (2006.01)

(52) U.S. Cl. .................... 427/304; 427/437; 427/443.1; 204/192.15

(58) Field of Classification Search ............ 204/192.12, 204/192.15; 427/304, 437, 443.1
See application file for complete search history.

(56) References Cited

U.S. PATENT DOCUMENTS

| | | |
|---|---|---|
| 4,345,985 A | 8/1982 | Tohda et al. |
| 4,372,824 A | 2/1983 | Toda et al. |
| 4,940,528 A | 7/1990 | Oki et al. |
| 5,766,672 A | 6/1998 | Hotta et al. |
| 6,025,205 A | 2/2000 | Park et al. |
| 6,054,331 A | 4/2000 | Park et al. |
| 6,254,926 B1 * | 7/2001 | Katafuchi et al. ........... 427/125 |

FOREIGN PATENT DOCUMENTS

| | | |
|---|---|---|
| EP | 1 180 681 A1 | 2/2002 |
| JP | 62-56978 B2 | 11/1987 |
| JP | 9-72876 | 3/1997 |
| JP | 10-312977 | 11/1998 |
| JP | 11-189880 * | 7/1999 |
| JP | 2001-124724 | 5/2001 |
| JP | 2001-188059 * | 7/2001 |
| JP | 2001-188059 A | 7/2001 |
| JP | 2002-107327 | 4/2002 |
| JP | 2002-231657 | 8/2002 |

OTHER PUBLICATIONS

Machine translation of 2001-188059 dated Jul. 2001.*
European Search Report for EP 03 02 5476 dated Mar. 10, 2004.

* cited by examiner

*Primary Examiner*—Rodney G McDonald
(74) *Attorney, Agent, or Firm*—Sughrue Mion, PLLC

(57) ABSTRACT

A process for manufacturing a gas sensor including a detecting element having an electrode containing a precious metal formed on a surface of a solid electrolyte, comprising: a first step of applying a nuclei of a precious metal having a catalyzing action on a gas to be measured; and a second step of growing the nuclei, wherein the first step uses a physical vapor deposition method.

10 Claims, 12 Drawing Sheets

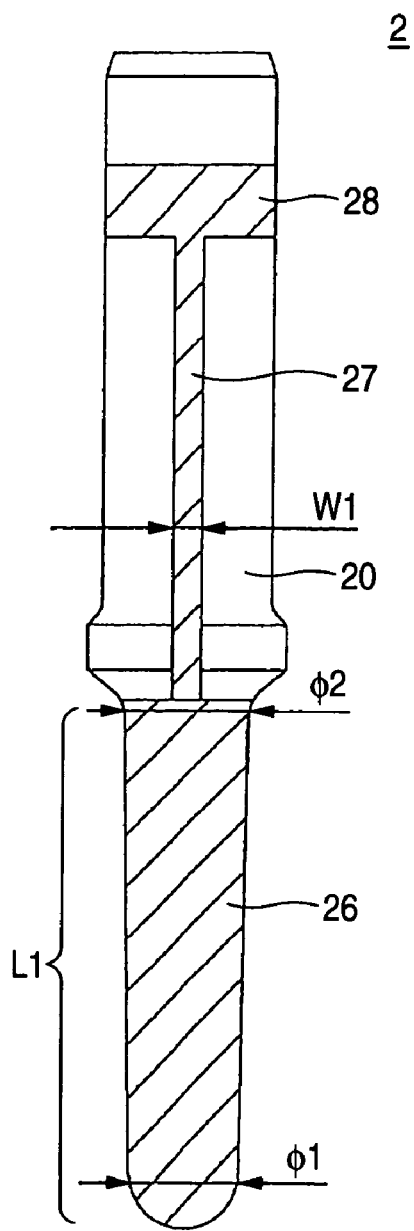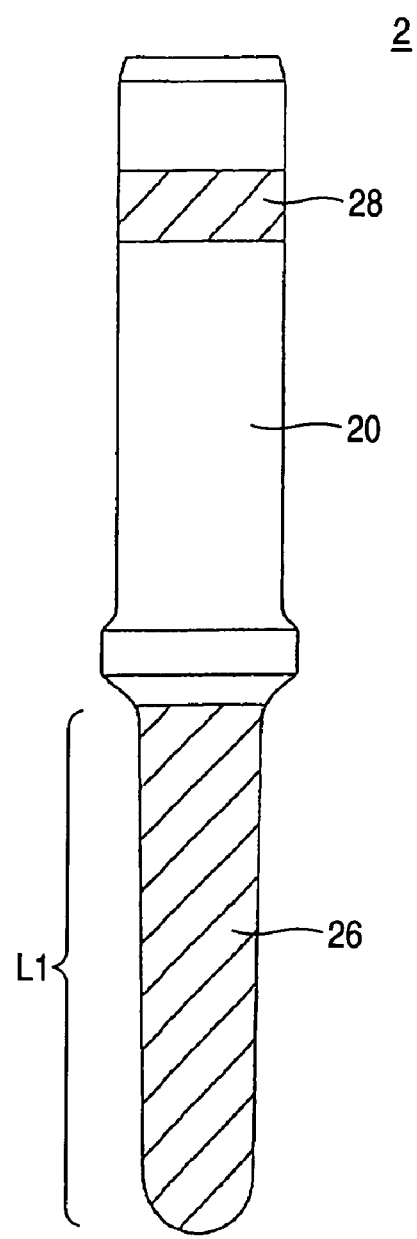

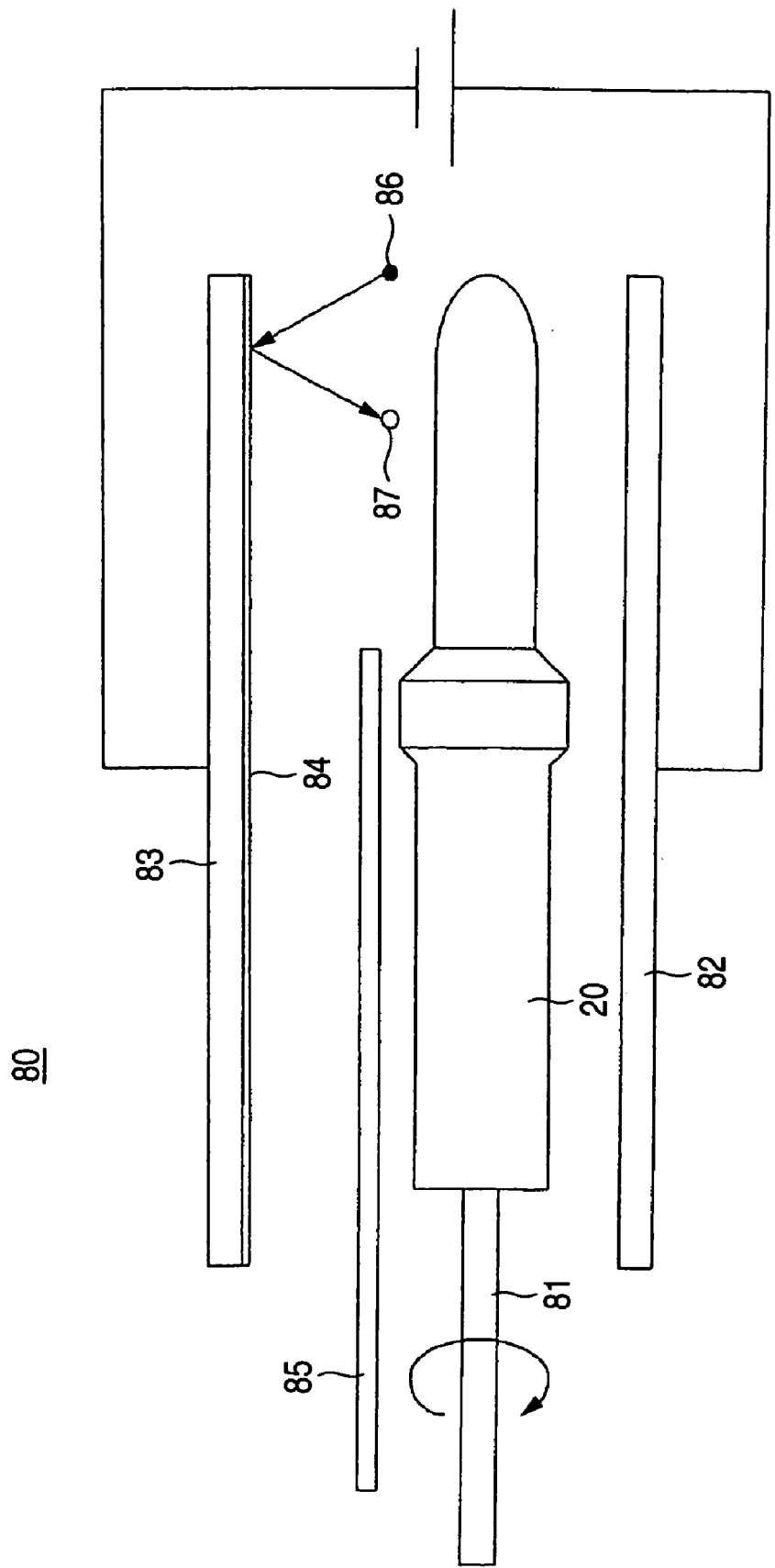

FIG. 5
FIG. 6
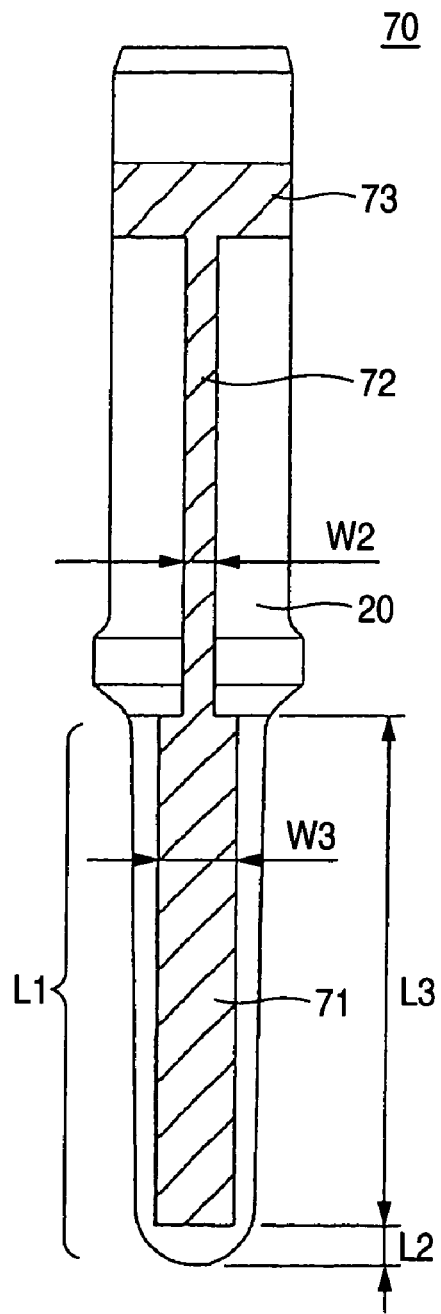
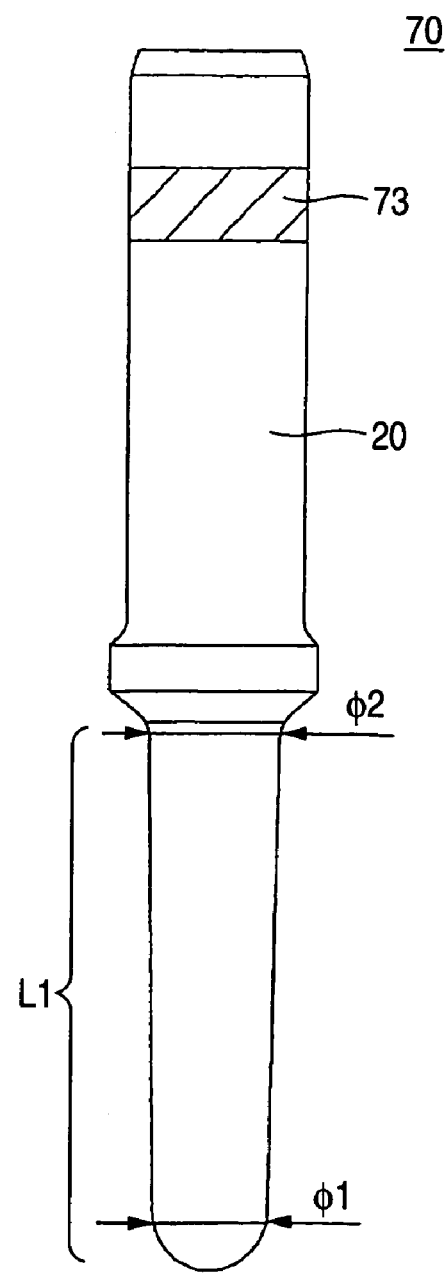

GAS SENSOR MANUFACTURING PROCESS

FIELD OF THE INVENTION

The present invention relates to a process for manufacturing a gas sensor including a detecting element having an electrode of a precious metal formed on the surface of a solid electrolyte.

BACKGROUND OF THE INVENTION

In the conventional art, there has been developed an oxygen sensor, which is provided with a detecting element having a detecting electrode and a reference electrode of platinum acting as an oxidation promoting catalyst formed on the outer wall and inner wall of a solid electrolyte (as will be called the "substrate") of a cylindrical shape having one end closed, so that it may detect an oxygen concentration on the principle of an oxygen concentration cell. This oxygen sensor is attached to the internal combustion engine of an automobile or the like so that it may be used for grasping the combustion state (or the A/F ratio) of the internal combustion engine.

Here, the detecting electrode of the detecting element in that oxygen sensor is formed through a nucleus depositing step of depositing the nuclei of platinum on the surface of the substrate and an electroless plating step of growing the deposited nuclei by an electrolessly plating method or an electrically plating method (as referred to JP-B-62-56978 (the term "JP-B" as used herein means an "examined Japanese patent publication"), for example).

First of all, at the nucleus depositing step (corresponding to the active point forming electrolessly plating step in JP-B-62-56978), the nuclei of platinum are deposited on the outer wall of the substrate by dipping the substrate in a container containing an aqueous solution of platinic ammine and by adding to this aqueous solution a reducer of sodium boron hydride (SBH) having a high reducing power. At this nucleus depositing step, however, at the time of dipping the substrate in the aqueous solution of platinic ammine, the portion of the outer wall of the substrate other than the desired one is coated with masking rubber so that the nuclei may not be deposited on the undesired portion.

At the end of the nucleus depositing step, moreover, the substrate is taken out from the container, and the masking rubber is removed. The substrate is rinsed to clear the outer wall of the substrate of the platinic ammine and the sodium boron hydride, and the process transfers to the nucleus growing step.

At the nucleus growing step (corresponding to the thin film electrolessly plating step and the thick film electric plating step in JP-B-62-56978 (pp. 3 to 4, FIG. 2)), like the nucleus depositing step, the substrate is dipped in the container containing the aqueous solution of platinic ammine, and a reducer of hydrazine having a weaker reducing power is added to that aqueous solution so that the nuclei deposited on the outer wall of the substrate may be gently grown to form the detecting electrode on the outer wall of the substrate. Here, at the nucleus growing step, the substrate is dipped in the plating liquid without being coated with the masking rubber.

SUMMARY OF THE INVENTION

Here, the oxygen sensor manufactured by the aforementioned manufacturing process has a problem that the detecting electrode of the detecting element fails to act sufficiently as the oxidation promoting catalyst thereby to cause a loss in the responding performances.

In the aforementioned detecting electrode, more specifically, the crystals of platinum after the nucleus growing step become coarse due to the large size of the nuclei deposited at the nucleus depositing step. Therefore, the number of intergranules of the platinum crystals is so small that the surface area (i.e., the surface area to act as the oxidation promotion catalyst) to contact with the exhaust gas is accordingly reduced.

As a result, it takes a long time for the oxygen existing in the vicinity of the detecting electrode to combine with the unburned contents (e.g., hydrocarbons or carbon monoxide) in the exhaust gas thereby to equilibrate the exhaust gas. Therefore, a delay occurs in the responsibility.

In the aforementioned manufacturing process, moreover, the sizes of the nuclei to be deposited become heterogeneous. Therefore, the thickness of the detecting electrode does not become uniform to cause a problem that the durable performances of the oxygen sensor are lost. In other words, the thinner portion of the detecting electrode sublimates earlier than the thicker portion.

In the aforementioned manufacturing process, moreover, the plating liquid flows in from the clearance, if formed between the masking rubber and the outer wall of the substrate, so that the nuclei are deposited on the portion other than the desired one. Therefore, a problem is that cares have to be troublesomely taken on the mounting of the masking rubber.

In order to solve the above-specified problems, therefore, the invention has an object to provide a process for manufacturing a gas sensor, which is excellent in responding performances and durable performances and which can form an electrode easily.

In order to achieve the above-specified object, according to the invention, a process for manufacturing a gas sensor including a detecting element having an electrode of a precious metal formed on the surface of a solid electrolyte, comprising: a first step of applying the nuclei of a precious metal having a catalyzing action on a gas to be measured; and a second step of growing said nuclei, wherein said first step uses a physical vapor deposition (PVD) method.

According to this gas sensor manufacturing process, the nuclei having the size of an atomic or molecular level can be applied to the surface of the solid electrolyte so that the crystals of the precious metal making the electrode can be made minute after the second step. In the gas sensor manufactured according to the invention, more specifically, the electrode of the detecting element has a number of intergranules of the crystals of the precious metal so that it has an accordingly larger surface area (i.e., a surface area to act as a catalyst) of the electrode to contact with the gas to be measured. In other words, the catalyzing action of the electrode can be improved by the invention thereby to provide a gas sensor having more excellent responding performances than those of the prior art.

According to the invention, moreover, the sizes of the nuclei are individually homogenized so that the electrode to be formed can have a uniform thickness. Therefore, it is possible to provide a gas sensor, which is more excellent durable performances than those of the prior art.

According to the invention, moreover, when the precious metal is to be deposited on the surface of the solid electrolyte, the evaporation of the precious metal can be prevented merely by arranging at least one of shielding plate and a shielding cover at a portion other than that to form an electrode. Therefore, the gas sensor can be troublelessly manufactured. By arranging at least one of the shielding plate and the shielding cover, moreover, an electrode of a desired shape can be easily formed on the surface of the solid electrolyte.

Here, the physical deposition method is preferably exemplified by the sputtering method. In this case, even if the precious metal has a high melting point, the nuclei of the precious metal having a catalyzing action can be easily deposited on the surface of the solid electrolyte.

Moreover, the sputtering is preferably done under a pressure of 5 to 10 Pa. This range may be defined because the residual gas to be ionized may fail to exist sufficiently for a pressure lower than 5 Pa whereas the glow discharge may not be done for a pressure higher than 10 Pa. But, the pressure range is variable due to a condition of a deposition apparatus, and therefore, the range is not essential for the invention.

And, the second step is preferably exemplified by the electrolessly plating method.

By using the electrolessly plating method, more specifically, the precious metal can be homogeneously deposited on the surface of the solid electrolyte. If the electroless plating is done by using the reducer having such a reducing power that the precious metal is not deposited on the portion other than that, to which the nuclei are applied, the nuclei can be homogeneously grown without depositing the precious metal at the portion other than that having the nuclei applied thereto. In other words, it is possible to form an electrode of a uniform thickness on the surface of the solid electrolyte.

Here, the plating liquid of the process of the prior art can be used if it satisfies the condition that the precious metal is not deposited on the portion other that, to which the nuclei are applied. In other words, it is possible to use such an aqueous solution of complex salt of platinum and a reducer as satisfy the above-specified condition. If an aqueous solution of platonic (IV) ammine or an aqueous solution of platinous (II) ammine is used as said aqueous solution of complex salt of platinum, and wherein hydrazine is used as said reducer, more specifically, the deposition rate can be optimized to satisfy the condition that the precious metal is not deposited on the portion other than that, to which the nuclei are applied.

If the plating is done by leaving the substrate, to which the nuclei of the precious metal were applied, to stand while being rocked in an electrolessly plating liquid, moreover, it is more effective to form the electrode having the uniform thickness.

BRIEF DESCRIPTION OF THE DRAWINGS

FIG. 2 is a lefthand side elevation of a detecting element 2 in FIG. 1;

FIG. 3 is a righthand side elevation of a detecting element 2 in FIG. 1;

FIG. 4 is a conceptional diagram schematically showing a nucleus applying step in the manufacture of the detecting element 2;

FIG. 5 is a top plan view showing the exterior of a detecting element 70 to be used in an oxygen sensor of a second embodiment;

FIG. 6 is a top plan view of the detecting element 70 on the back side of FIG. 5;

DETAILED DESCRIPTION OF THE INVENTION

Embodiments of the invention will be described in the following with reference to the accompanying drawings.

First Embodiment

Figure 1:
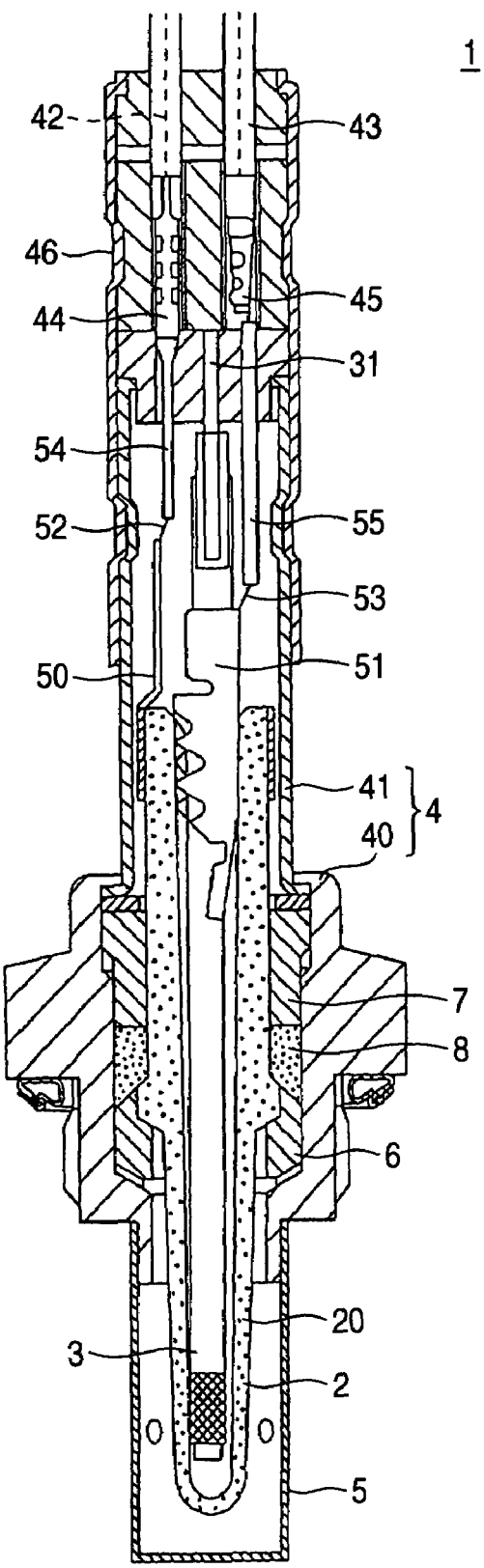
FIG. 1 is a sectional view showing the entire construction of an oxygen sensor 1 of a first embodiment.

First of all, FIG. 1 is a sectional diagram showing the entire construction of an oxygen sensor, which is manufactured by applying the invention thereto.

As shown in FIG. 1, an oxygen sensor 1 is constructed to include: a detecting element 2 made of a cylindrical substrate 20 composed mainly of zirconia and having one end closed; a rod-shaped ceramic heater (as will be shortly called the "heater") 3 arranged in the detecting element 2; a casing for housing those detecting element 2 and heater 3; and a cylindrical protector 5 mounted on the lower end portion of the casing 4 for covering such a bottom portion (i.e., the closed one end) of the detecting element 2 as is protruded from the lower end portion of the casing 4.

Here, the casing 4 is constructed to include: a main fixture 40 for fixing the detecting element 2 in the casing 4 with annular ceramic holders 6 and 7 and ceramic powder 8 housed therein, and for fixing the oxygen sensor 1 on the exhaust pipe or the like of an internal combustion engine; and a cylindrical outer tube 41 extending upward of the main fixture 40 for introducing the atmosphere downward into the detecting element 2.

On the inner wall and outer wall of the upper end portion of the detecting element 2, respectively, there are mounted terminal fixtures 50 and 51 for extracting an electromotive force from the detecting element 2. With these terminal fixtures 50 and 51, respectively, through lead wires 52 and 53, there are connected connecting terminals 54 and 55, which are protruded from the upper end portions of the outer tube 41. With the upper end portion of the heater 3, moreover, there is connected a connecting terminal 31, which is protruded from the upper end portion of the outer tube 41. Here, the heater 3 is fixed by the terminal fixture 51 in the detecting element 2 and is brought, by the leftward pushing force from the terminal fixture 51, into contact with the inner circumference wall of the portion extending from the axially central portion to the bottom portion of the detecting element 2.

On the upper end portion of the outer tube 41, moreover, there is caulked a cylindrical protecting outer tube 46. This outer tube 46 is provided with: signal wires 42 and 43 for extracting the electromotive force generated by the detecting element 2; power lines (although not shown) for supplying the electric force to the heater 3; female terminals 44 and 45 for connecting the signal wires 42 and 43 and the connecting terminals 54 and 55; and female terminals (although not shown) for connecting the power lines and the connecting terminal 31. The electromotive force of the detecting element 2 is extracted to the outside, and the electric power is supplied from the outside to the heater 3.

Here, FIG. 2 is a lefthand side elevation of the detecting element 2 in FIG. 1, and FIG. 3 is a righthand side elevation of a detecting element 2 in FIG. 1.

As shown in FIGS. 2 and 3, the detecting element 2 is formed by covering the outer wall of such a portion L1 with a detecting electrode 26 of platinum while making one round of the outer circumference of the substrate 20, as extends from the leading end of the bottom portion and to the vicinity of the axially central portion of the substrate 20. Here, this detecting electrode 26 is coated on its surface with powder of spinel ($MgAl_2O_4$) (although not shown), thereby to protect the detecting electrode 26 against the heat of the exhaust gas.

On the outer wall in the vicinity of the upper end portion of the substrate 20, moreover, there is formed a band-shaped terminal connecting portion 28, which makes one round of the outer circumference of the substrate 20, thereby to connect the terminal fixture 50.

Between the detecting electrode 26 and the terminal connecting portion 28, on the other hand, there is formed along the axial direction of the substrate 20 one long lead portion 27, which has a sufficiently narrower width W1 than that of the detecting electrode 26 and through which the detecting electrode 26 and the terminal connecting portion 28 are electrically connected.

All over the inner wall of the substrate 20, there is formed a reference electrode (although not shown), which is made of platinum like that of the detecting electrode 26.

A process for manufacturing the detecting element 2 will be described in detail in the following.

At first, the substrate 20 is prepared by pressing a solid electrolyte composed mainly of zirconia into a cylindrical shape having one end closed, and then by sintering the cylindrical shape by exposing it to the atmosphere of 1,500° C. for 2 hours. At the sintering time, a platinum paste is printed in advance on the portions to form the lead portion 27 and the terminal connecting portion 28, and these lead portion 27 and terminal connecting portion 28 are formed at the time of sintering the solid electrolyte.

Next, the detecting electrode 26 is formed on the prepared substrate 20.

In order to form the detecting electrode 26, a nucleus applying step of depositing the nucleus of platinum on the outer wall of the portion L1 of the substrate 20 is performed by using Ion Coater of IB-3 manufactured by Eikoh Kabushiki Gaisha. Here, the Ion Coater is an apparatus for ionizing the residual gas (or air) by making a glow discharge in a low vacuum region (at 5 to 10 Pa) and for sputtering the atoms or molecules composing a target (i.e., platinum foil) by causing the ions of the residual gas to collide against the target.

Here, FIG. 4 is a conceptional diagram schematically showing the nucleus applying step.

At the nucleus applying step, as shown in FIG. 4, a support rod 81 is inserted at first into the substrate 20 to support the substrate 20 in parallel with the plane of a positive electrode 82 in an ion coater 80. Subsequently, a shielding plate 85 is so arranged between the substrate 20 and a platinum foil (i.e., target) 84 disposed on a negative electrode 83 of the ion coater 80 as to cover only that portion (i.e., the portion above the portion L1 in FIGS. 2 and 3) in the substrate 20, on which the detecting electrode 26 is not formed.

After the pressure of the residual gas in the ion coater 80 was set at about 8 Pa, a voltage is so applied for 5 minutes between the positive electrode 82 and the negative electrode 83 of the ion coater 80 as to make a current value of about 6 mA, so that ions 86 of the residual gas may collide against the platinum foil 84 to deposit nuclei 87 of the platinum atoms, as hit from the platinum foil 84, on the substrate 20. In order to deposit the platinum nuclei on the whole portion L1 of the substrate 20, however, the substrate 20 is turned for each deposition by 120 degrees on the support rod 81, and this turn is repeated totally three times.

When the nucleus applying step is thus ended, the manufacturing process transfers to a nucleus growing step of growing the nuclei, as deposited on the substrate 20, by an electrolessly plating method.

At this nucleus growing step, the substrate 20 is heated at first while being dipped in an aqueous solution of complex salt of platinum. Next, an aqueous solution of hydrazine (in concentration: 85 wt. %) is added to the aqueous solution of complex salt of platinum dipping the substrate 20 is added, and the substrate 20 is left to stand in the electrolessly plating liquid for 2 hours while being rocked, so that the platinum nuclei deposited on the substrate 20 may grow to form the detecting electrode 26 on the outer wall of the substrate 20. Here, the concentration of the aqueous solution of complex salt of platinum is so adjusted that the thickness of the electrolessly plated platinum may have a thickness of 1.2 μm.

In order to stabilize the detecting electrode 26, moreover, a heat treatment is done at 1,200° C. for 1 hour, and spinel powder is applied by a plasma spray coating method to the surface of the detecting electrode 26 thereby to form a protective layer (although not shown).

Subsequently, the reference electrode is formed on the substrate 20.

In order to form the reference electrode, the substrate 20 is left to stand while hydrofluoric acid (in concentration: 5 wt. %)being injected into the substrate 20. And, the substrate 20 is rinsed by spraying water thereinto, and is then dried.

Next, an aqueous solution of chloroplatinic acid (a platinum concentration: 0.5 g/m$^3$) is injected into the substrate 20 and is heated. After this, the chloroplatinic acid is discharged to form the coating film of an aqueous solution of chloroplatinic acid on the inner wall of the substrate 20. Subsequently, an aqueous solution of hydrazine (in a concentration: 5 wt. %) is injected into the substrate 20, and is heated to 75° C. and left to stand for 30 minutes thereby to deposit the nuclei of platinum on the inner wall of the substrate 20.

When the deposition of the nuclei is ended, the aqueous solution of chloroplatinic acid is discharged. An electrolessly plating liquid, which has been prepared by mixing an aqueous solution of complex salt of platinum (a platinum concentration: 15 g/m$^3$) and an aqueous solution of hydrazine (in a concentration: 85 wt. %), is injected into the substrate 20, and is heated and left to stand so that the nuclei grow to form the reference electrode.

And, the substrate 20 having the reference electrode formed therein is rinsed by spraying water into its inside, and is put into a driver so that it is sufficiently dried.

Finally, the substrate 20 is aged in a combustion gas to activate the electrode so that the detecting element 2 is obtained.

In the oxygen sensor 1 having the detecting element 2 thus manufactured, the sputtering method is used at the nucleus applying step when the detecting electrode 26 of the detecting element 2 is formed, so that the detecting electrode 26 formed after the nucleus growing step has a number of intergranules of crystals of platinum. In other words, the surface area (i.e., the surface area to act as a catalyst) of the detecting electrode 26 to contact with oxygen is larger than that of the prior art so that the catalyzing action of the detecting electrode 26 becomes higher than that of the prior art. Therefore, the oxygen sensor 1 can exhibit more excellent responding performances than that of the prior art.

By the manufacturing process thus far described, moreover, the sizes of the nuclei are individually homogenized so that the detecting electrode 26 has a uniform thickness. Therefore, the oxygen sensor 1 exhibits a more excellent durability than that of the prior art.

When the nuclei of platinum are to be deposited on the substrate of the detecting element 2, moreover, the platinum nuclei can be prevented merely by arranging the shielding plate from being deposited on the substrate other than the portion L1, on which the detecting electrode 26 is to be formed. It is, therefore, possible to manufacture the oxygen sensor 1 without any trouble.

In short, according to the manufacturing process of the invention, it is possible to manufacture the gas sensor, which is more excellent in the responding performances and the durable performances than the prior and which can form the electrode easily.

According to the manufacturing process of this embodiment, moreover, the electrolessly plating method is used at the nucleus growing step when the detecting electrode 26 is formed. Therefore, the detecting electrode 26 can be formed more quickly than that, in which the nuclei are grown by continuing the sputtering from the nucleus applying step.

Second Embodiment

Here will be described a second embodiment.

In the oxygen sensor of this embodiment, the detecting element 2 of the oxygen sensor 1 of the first embodiment is replaced by a detecting element 70, as shown in FIGS. 5 and 6.

Therefore, the following description is directed exclusively to the detecting element 70. Here, FIG. 5 is a top plan view showing the exterior of the detecting element 70, and FIG. 6 is a top plan view of the detecting element 70 on the back side of FIG. 5.

Like the detecting element 2, the detecting element 70 is constructed to include the substrate 20, as shown in FIGS. 5 and 6. On the outer wall of the portion L1 of the substrate 20, moreover, there is formed such a long-size detecting electrode 71 upward of the substrate 20 from the upper portion at a distance L2 from the bottom portion of the substrate 20, as has a width W3 smaller than the diameter at the portion L1 of the substrate 20 and a length L3 (L3<L1). However, the outer wall of the portion L1 of the substrate 20 is so coated with powder of spinel (although not shown) as to cover the detecting electrode 71.

In the detecting element 70, as in the detecting element 2, there is formed on the outer wall near the upper end portion of the substrate 20 a band-shaped terminal connecting portion 73, which makes one round of the outer circumference of the substrate 20 thereby to connect the terminal fixture 50.

Between the detecting electrode 71 and the terminal connecting portion 73, moreover, there is formed along the axial direction of the substrate 20 one long-size lead portion 72, which has a width W2 narrower than the detecting electrode 71 so that the detecting electrode 71 and the terminal connecting portion 73 are electrically connected therethrough.

Here, the reference electrode (although not shown) of the detecting element 70 is formed, as in the detecting element 2, all over the inner wall of the substrate 20.

The detecting element 70 thus constructed is so mounted in the oxygen sensor as to bring the heater 3 into contact with the inner circumference wall, as opposed to the detecting electrode 71, of the substrate 20.

In order to manufacture the detecting element 70, there may be a process similar to that for manufacturing the detecting element 2. At the time of forming the detecting electrode 71, however, there is arranged between the substrate 20 and the platinum foil disposed on the negative electrode of the ion coater a shielding plate, which has an area for covering the substrate 20 as a whole and which has such a through hole at a portion to form the detecting element 71 as has a planar shape congruent with the detecting electrode 71. Unlike the first electrode, moreover, the sputtering is done for 5 minutes while leaving the substrate 20 to stand on the support rod.

The oxygen sensor of this embodiment having the detecting element 70 thus constructed can attain effects like those of the oxygen sensor 1 of the first embodiment. In the detecting element 70, moreover, the detecting electrode 71 is formed exclusively at the portion, in which the solid electrolyte is the most active and with which the heater contacts, of the detecting element 70. Therefore, the oxygen sensor of this embodiment exhibits better responding performances than those of the oxygen sensor 1 of the first embodiment.

EXAMPLES

Here, we have performed experiments so as to demonstrate the effects of the oxygen sensors of the first and second embodiments thus far described. In these demonstration experiments: the responding performances and the performances of durability against the heat were compared by causing the oxygen sensor 1 having the detecting element 2 to belong to Example 1, the oxygen sensor having the detecting element 70 to Example 2, and the oxygen sensor having the detecting element (although not shown) of the prior art to Example 1.

Here, the detecting element of the prior art is manufactured by using the process of the prior art but is set to have the shapes and sizes of the substrate and electrode absolutely like those of the detecting element 2.

In these demonstration experiments, the portion L1 of the detecting elements 2 and 70 from the axial center to the bottom portion has a length set at 22.0 mm, and the lower portion and the upper portion of L1 have diameters $\phi 1$ and $\phi 2$ set at 5.0 mm and 6.0 mm, respectively. Moreover, the lead portions 27 and 72 of the detecting elements 2 and 70 have their widths W1 and W2 set to 1.5 mm and have their thickness set to 10 μm.

Moreover, the distance L2 from the bottom portion of the detecting element 70 to the detecting electrode 71 is set at 2.0 mm, and the detecting electrode 71 has its length L3 set at 20.0 mm.

In both the detecting elements, on the other hand, the detecting electrodes have a thickness set to 1.2 μm, and the spinel coated on the portion L1 has a thickness set at 200 μm.

Here will be described the process of the prior art for manufacturing the detecting element. This manufacturing process of the prior art is absolutely similar to those of the first and second embodiments, excepting the nucleus applying step of forming the detecting electrode.

In order to apply the nuclei to the detecting electrode, masking rubber is so mounted at first on the substrate as to cover the substrate excepting the portion to form the detecting electrode. Then, the substrate having the masking rubber mounted thereon is dipped in an aqueous solution of complex salt of platinum (a platinum concentration: 15 g/m$^3$). Subsequently, the aqueous solution of platinum complex salt dipping the substrate is heated to 60° C., and an aqueous solution of sodium borate is added. Moreover, the substrate is left to stand in this mixture liquid while being rocked, to deposit the nuclei of platinum on the outer wall of the substrate.

After this nucleus deposition, moreover, the detecting element of the prior art is obtained through the nucleus growing step like that of the detecting elements 2 and 70 of the first and second embodiments.

The results of our demonstration experiments are presented in FIG. 7 to FIG. 12.

Figure 7:
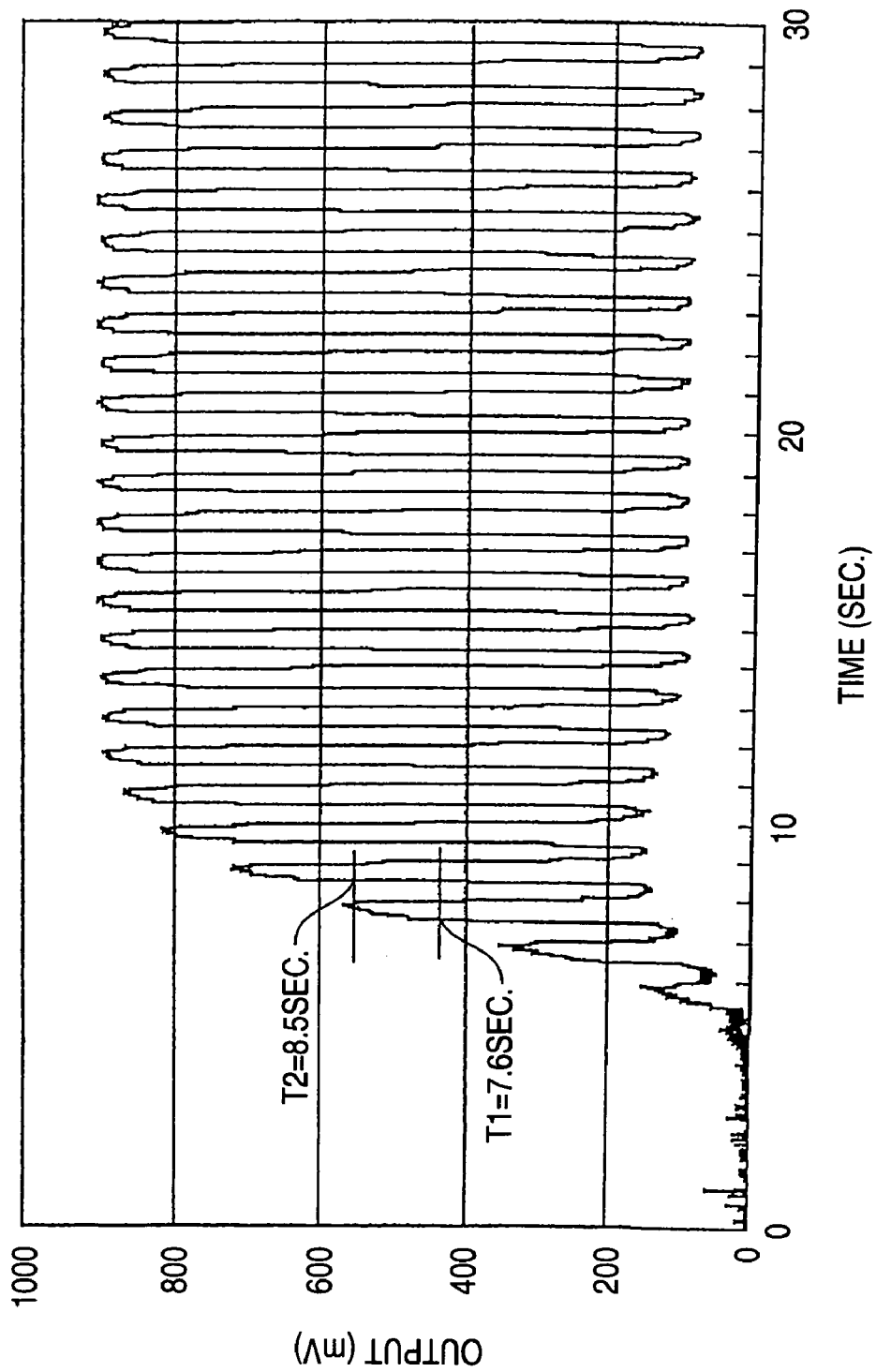
FIG. 7 is a waveform diagram of the output of an oxygen sensor 1, as recorded just after an electric power was supplied to the heater of the oxygen sensor of Example 1.
Figure 8:
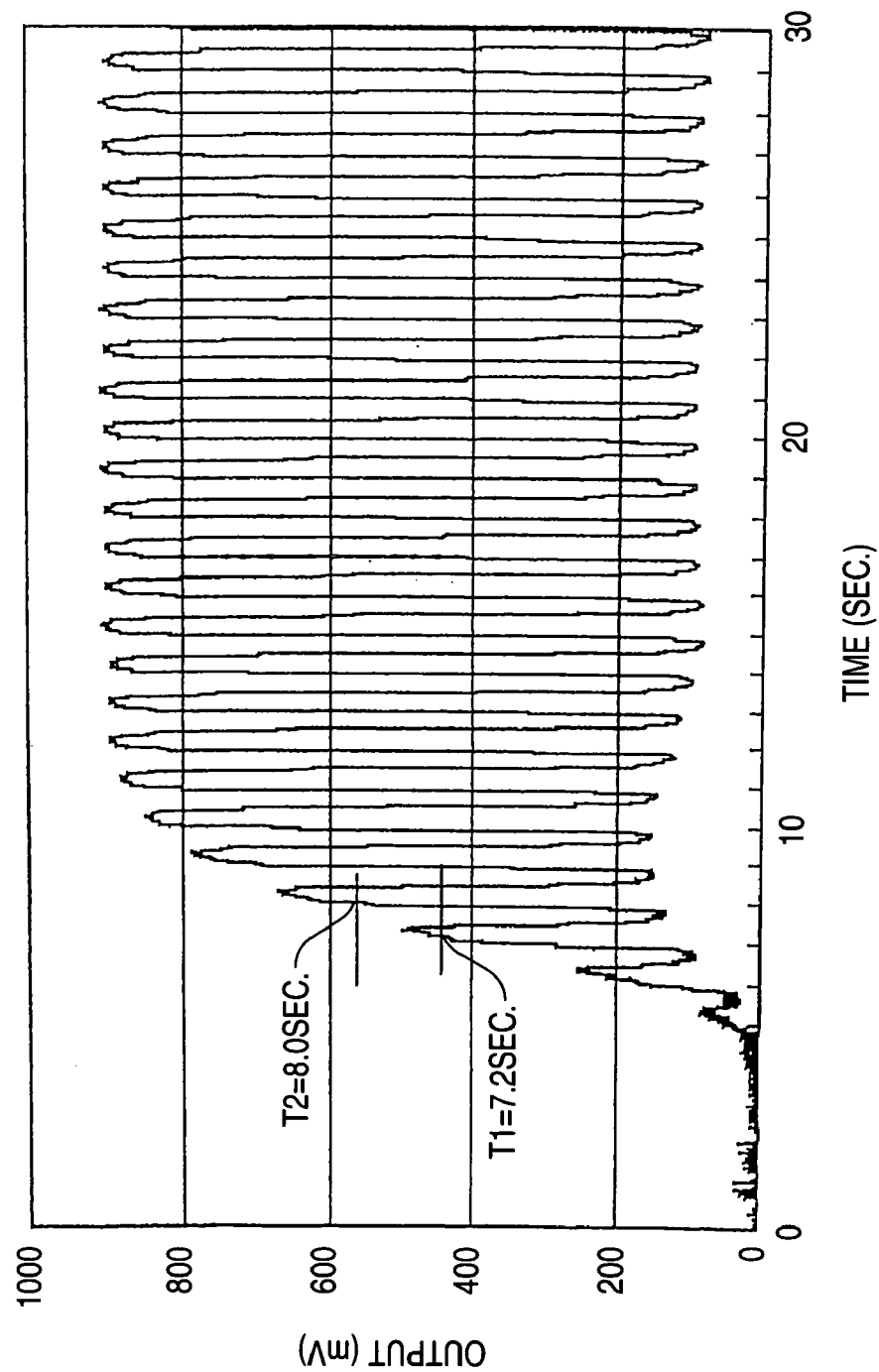
FIG. 8 is a waveform diagram of the output of an oxygen sensor 1, as recorded just after an electric power was supplied to the heater of the oxygen sensor of Example 2.
Figure 9:
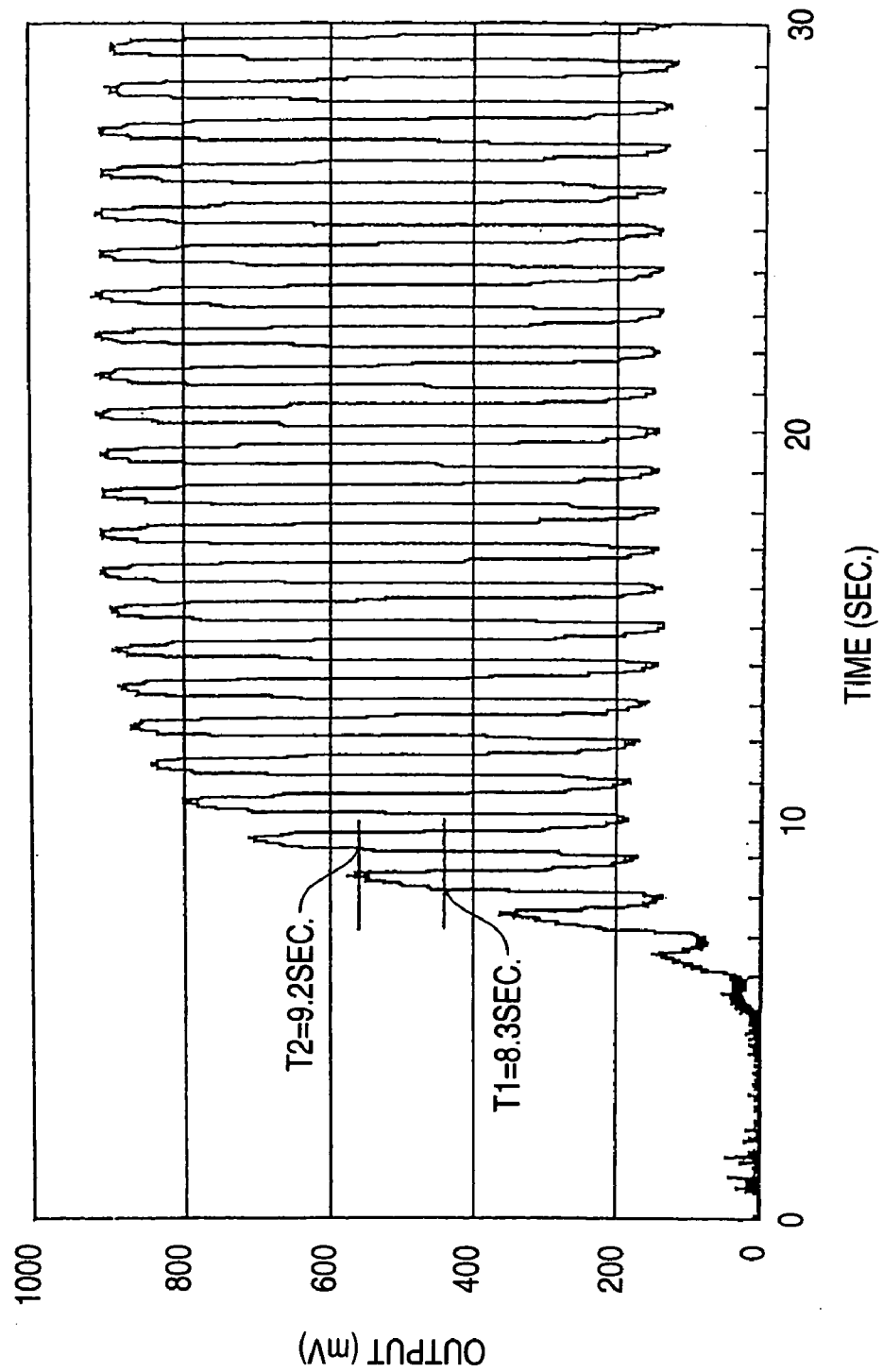
FIG. 9 is a waveform diagram of the output of an oxygen sensor 1, as recorded just after an electric power was supplied to the heater of the oxygen sensor of Comparison 1.

First of all, FIG. 7 to FIG. 9 are waveform diagrams of those outputs of the individual oxygen sensors, which were recorded when the aforementioned three oxygen sensors were sequentially mounted on the common internal combustion engine and when the A/F ratio of the internal combustion engine was alternately switched from lean to rich and from rich to lean for a period of 2 Hz. Here: FIG. 7 is the output waveform diagram of the oxygen sensor of Example 1; FIG. 8 is the output waveform diagram of the oxygen sensor of Example 2; and FIG. 9 is the output waveform diagram of the oxygen sensor of Comparison 1.

Here in FIG. 7 to FIG. 9, reference letter T1 designates the time period till the output of the oxygen sensor, as recorded just after the electric power was supplied to the heater of the oxygen sensor, acquires an amplitude to exceed a threshold value (e.g., 450 mV) at the boundary between the rich and the lean. And, reference letter T2 designates the time period till the output of the oxygen sensor exceeds the threshold value at first just after the electric power was supplied to the heater of the oxygen sensor, reaches again the threshold value in accordance with the change in the A/F ratio of the internal combustion engine, and reaches a predetermined value (e.g., 550 mV) set higher than the threshold value. Here, the letter T1 indicates the time period till the detecting element of the oxygen sensor is activated, and the letter T2 indicates the time period till a stable output is obtained from the detecting element.

In the oxygen sensors of Examples 1 and 2 according to the invention, as presented in FIG. 7 and FIG. 8, the time period T1 had values of 7.6 seconds and 7.2 seconds, respectively, and the time period T2 had values of 8.5 seconds and 8.0 seconds, respectively. In the oxygen sensor of Comparison 1, as presented in FIG. 9, on the contrary, the time periods T1 and T2 had values of 8.3 seconds and 9.2 seconds, respectively.

From these results, it can be confirmed that the oxygen sensors of Examples 1 and 2 can be activated for shorter time periods to generate stable outputs quickly than the oxygen sensor of Comparison 1 manufactured by the process of the prior art.

Figure 10:
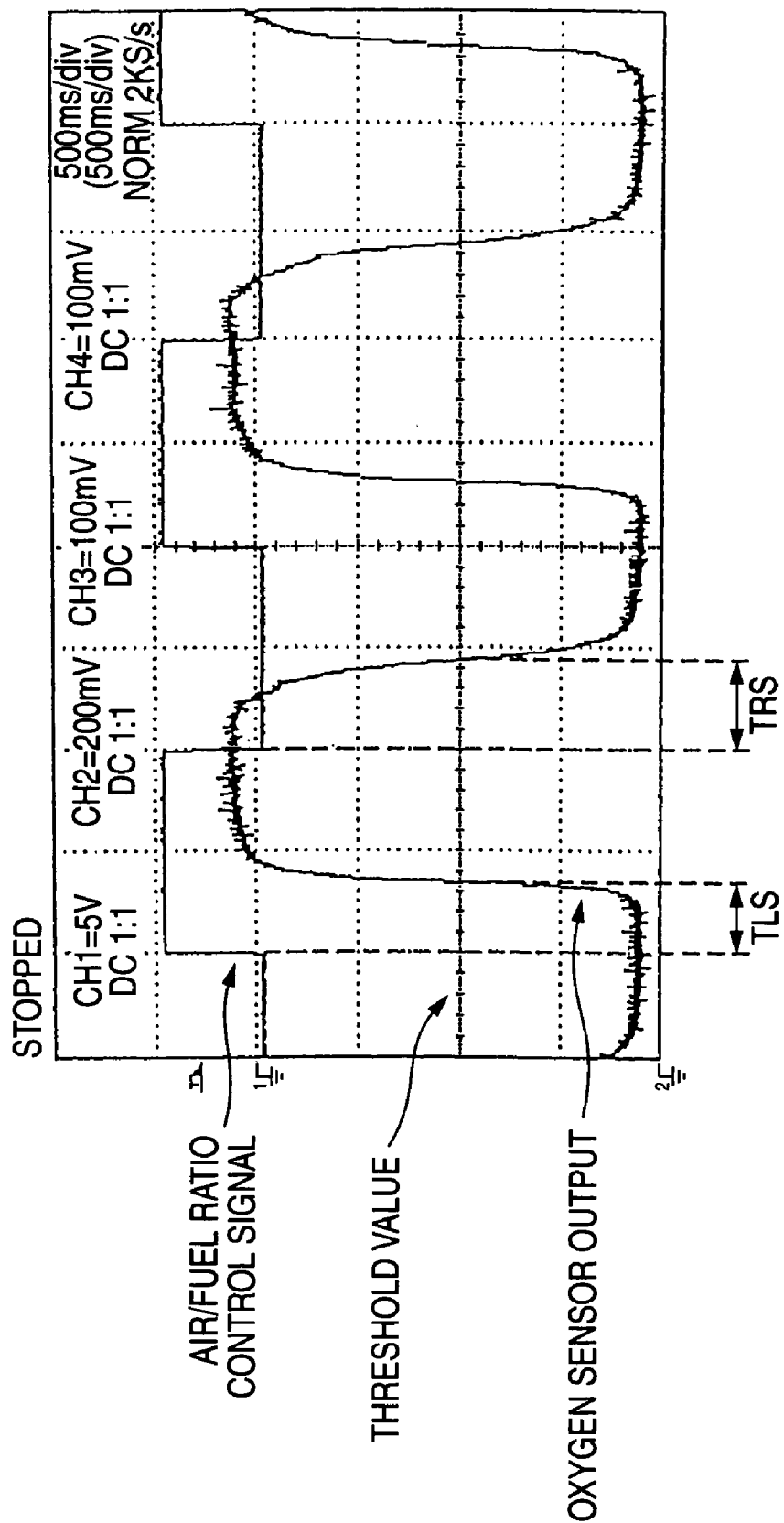
FIG. 10 is a waveform diagram of the output of the oxygen sensor of Example 1 against the change in an A/F ratio control signal.
Figure 11:
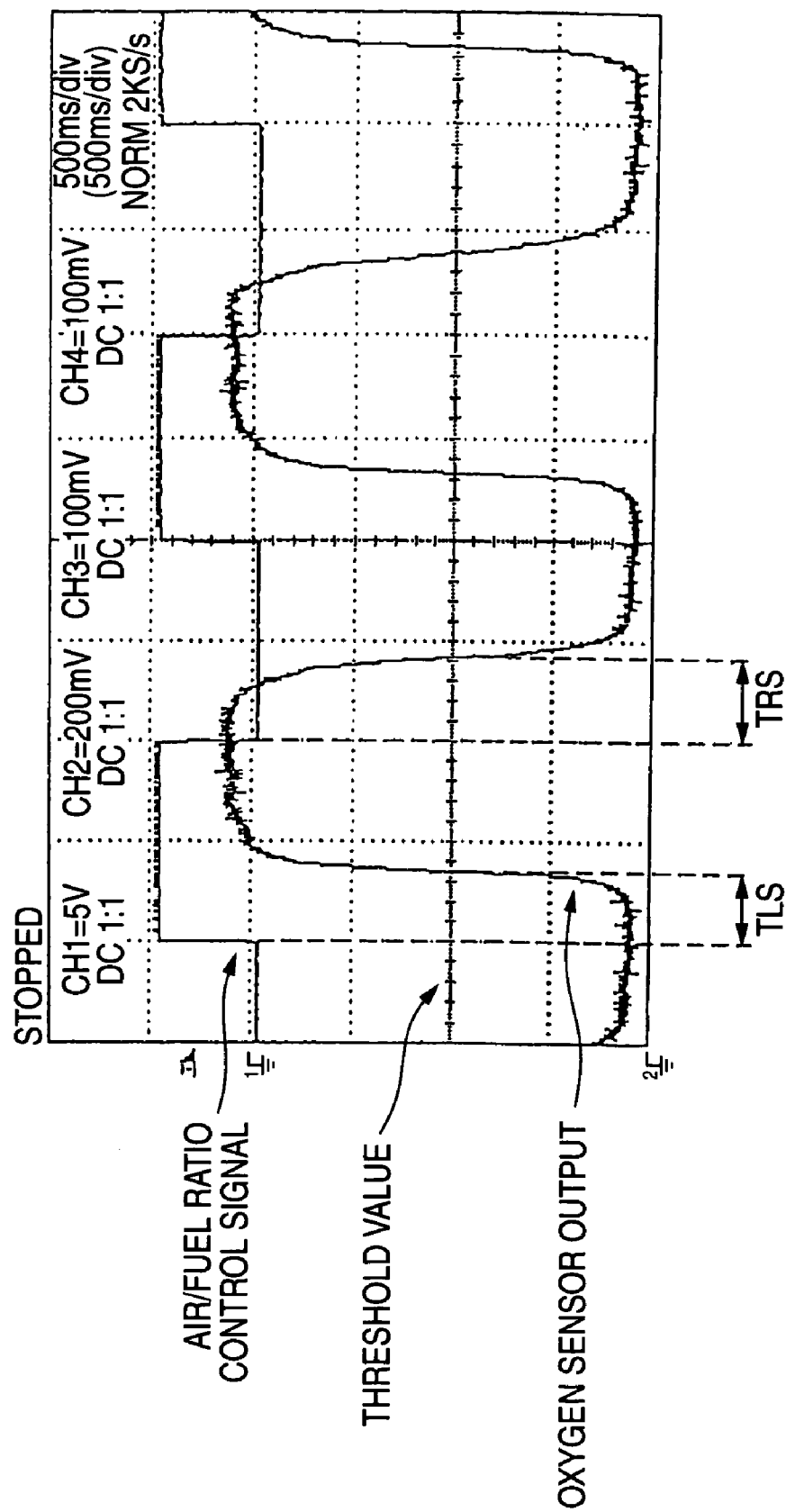
FIG. 11 is a waveform diagram of the output of the oxygen sensor of Example 2 against the change in an A/F ratio control signal.
Figure 12:
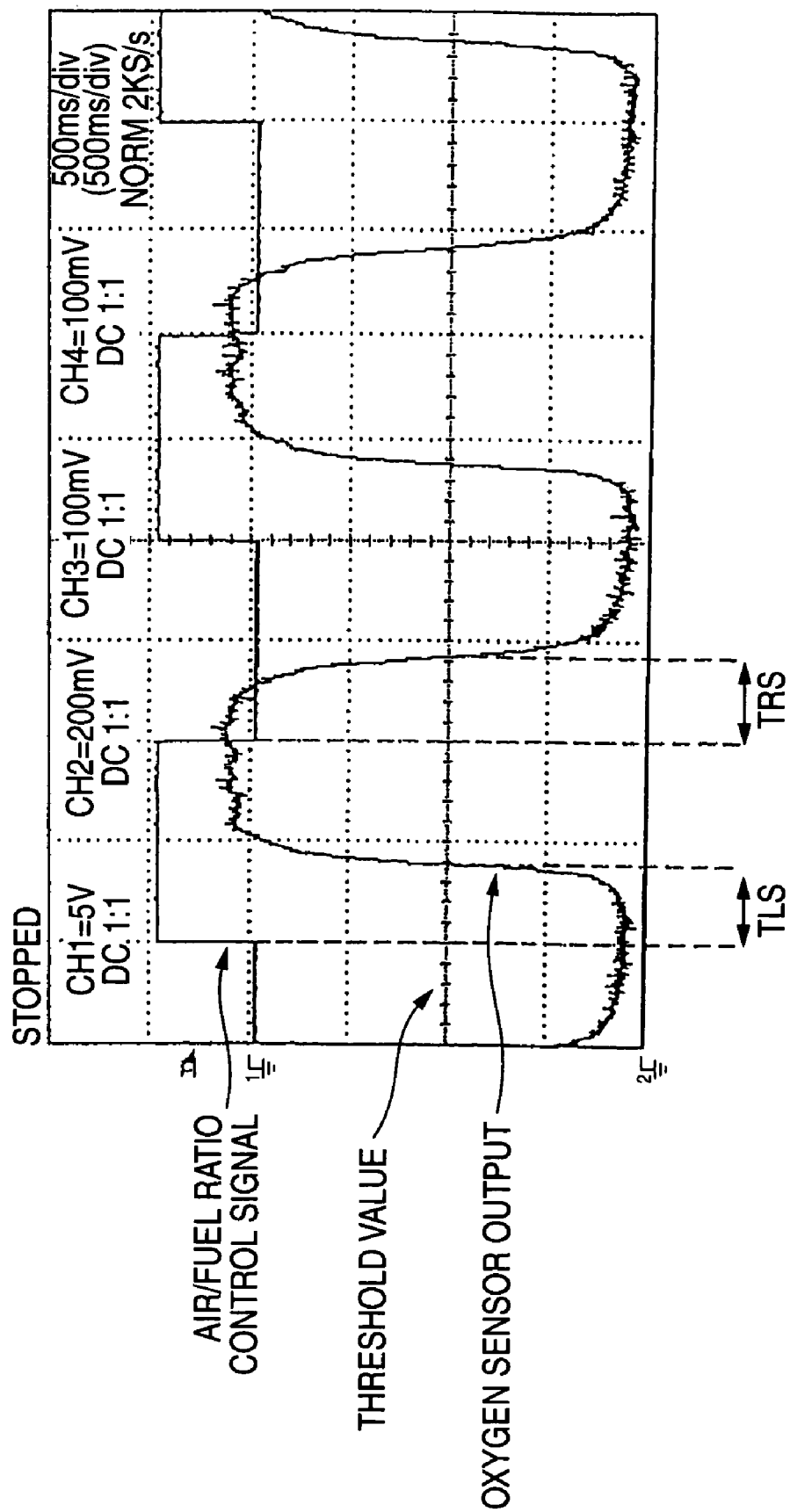
FIG. 12 is a waveform diagram of the output of the oxygen sensor of Comparison 1 against the change in an A/F ratio control signal.

Next, FIG. 10 to FIG. 12 are waveform diagrams, which are recorded of the outputs of the aforementioned individual oxygen sensors against the change in the A/F ratio control signal for controlling the A/F ratio of the internal combustion engine. Here: FIG. 10 is the waveform diagram of the oxygen sensor 1 of Example 1; FIG. 11 is the waveform diagram of the oxygen sensor 1 of Example 2; and FIG. 12 is the waveform diagram of the oxygen sensor 1 of Comparison 1.

Here in FIG. 10 to FIG. 12, reference letters TLS designate a time period till the outputs of the individual oxygen sensors exceed a threshold value after the A/F ratio control signal was switched from the lean to the rich, and reference letters TRS designate a time period till the outputs of the individual oxygen sensors fall below the threshold value after the A/F ratio control signal was switched from the rich to the lean.

In the oxygen sensors of Examples 1 and 2, as presented in FIG. 10 and FIG. 11, the time period TLS had values of 0.323 seconds and 0.319 seconds, respectively, and the time period TRS had values of 0.307 seconds and 0.305 seconds, respectively. In the oxygen sensor of Comparison 1, as presented in FIG. 12, on the contrary, the time periods TLS had a value of 0.343 seconds, and the time period TRS had a value 0.324 seconds.

From these results, it can be confirmed that the oxygen sensors of Examples 1 and 2 have quicker responses to the fluctuation in the oxygen concentration in the exhaust gas than the oxygen sensor of Comparison 1.

From these results, it has been verified that the oxygen sensors of Examples 1 and 2 can exhibit satisfactory responding performances.

Here, the aforementioned individual oxygen sensors were exposed for 2,000 hours to the exhaust gas at 1,000° C., and the changes in the outputs of the individual oxygen sensors were confirmed against the change in the A/F ratio control signal for controlling the A/F ratio of the internal combustion engine.

As a result, the oxygen sensor of Comparison 1 was broken at the detecting electrode so that it did not generate no output. On the contrary, the responding time periods (TRS+TLS) of the oxygen sensors of Examples 1 and 2 were 0.661 seconds and 0.650 seconds, respectively.

From these results, it has been verified that both the oxygen sensors of Examples 1 and 2 are neither broken in the detecting electrodes nor seriously changed in the responding performances even if they are exposed for a long time to the atmosphere at a high temperature, so that they have high durable performances against the heat.

At the time of manufacturing the detecting elements individually, as used in the comparison experiments, the Inventors have measured the sizes of platinum crystals constructing the detecting electrodes. As a result, the platinum crystals constructing the detecting electrode had a size of about 0.2 to 0.3 μm. However, the detecting electrode 26 of the detecting electrode 2 and the detecting electrode 71 of the detecting element 70 had such fine platinum crystals as could not be found, even if observed by setting the magnitude of a scanning type electronic microscope (SEM) at 20,000 times.

In short, according to the manufacturing process of the invention, the platinum crystals constructing the detecting electrode can be made fine. Therefore, the intergranules of the platinum crystals in the detecting electrode become so numerous that the surface area of the detecting electrode to contact with the exhaust gas can be made larger than that of the prior art.

Although the invention has been described hereinbefore in connection the embodiments, it should not be limited thereto in the least but can naturally take a variety of modes so far as it belongs to the present invention.

In the foregoing embodiments, for example, the invention has been applied to the manufacture of the oxygen sensor but may also be applied to the manufacture of another mode such as a nitrogen oxide ($NO_x$) sensor.

In the foregoing embodiments, moreover, platinum was used to form the detecting electrodes or the reference electrodes but may also be replaced by rhodium, palladium, silver or gold.

Moreover, the foregoing embodiments have used the DC glow discharge sputtering method at the nucleus applying step but may also use another sputtering method such as a magnetron sputtering method or an ion beam sputtering method, or a deposition method such as a vacuum evaporation method, a molecular beam deposition method, an ion plating method or an ion beam deposition method.

In the foregoing embodiments, moreover, at the nucleus applying step for forming the detecting electrode 26 of the detecting element 2, the substrate 20 is turned for every predetermined time periods. However, the nuclei of platinum may also be deposited by turning the substrate 20 at all times or by methods, as shown in FIG. 13 and FIG. 14.

Figure 13:
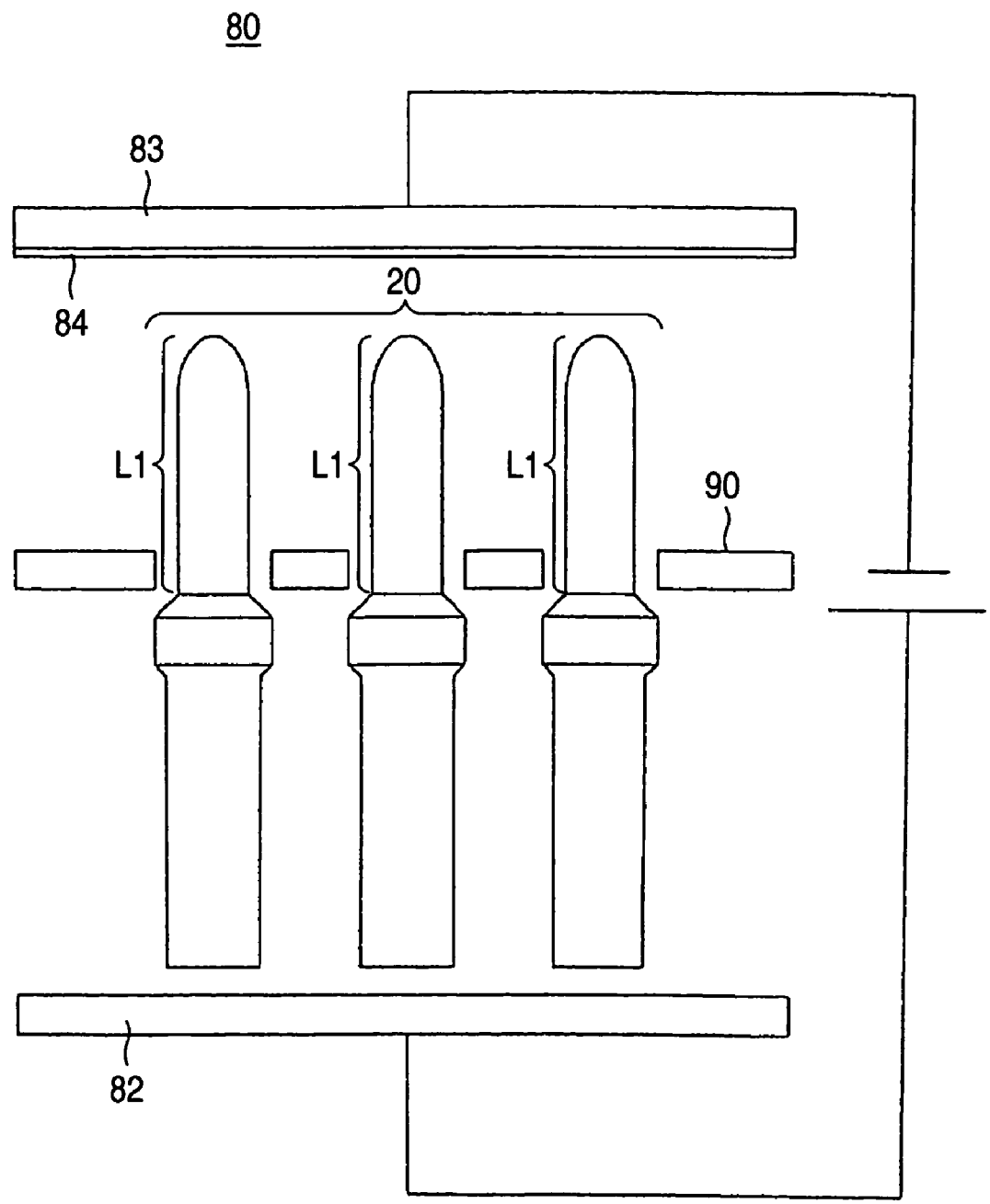
FIG. 13 is a schematic diagram showing a modification of the nucleus applying step in Embodiments 1 and 2.
Figure 14:
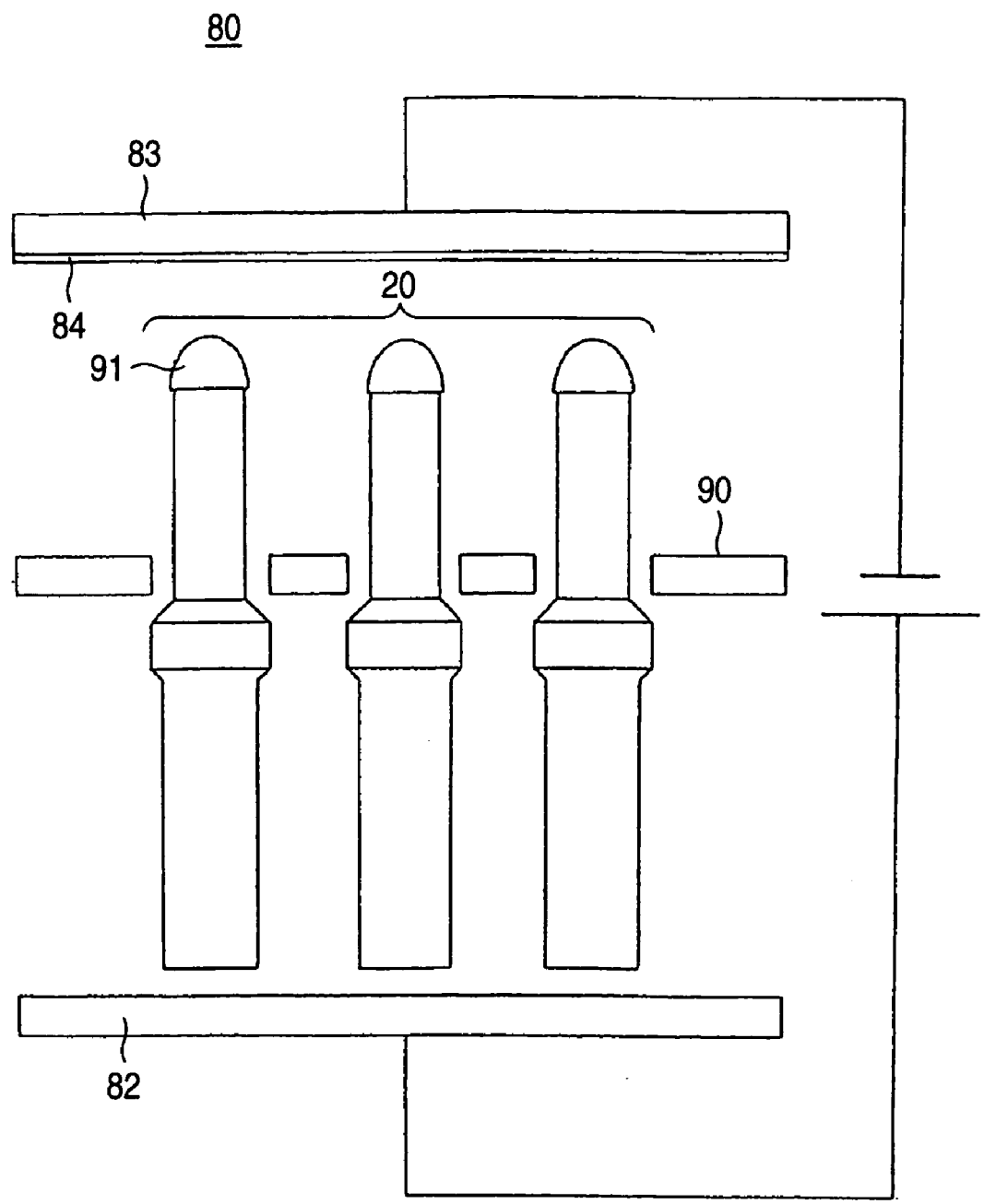
FIG. 14 is a schematic diagram showing a modification of the nucleus applying step in Embodiments 1 and 2.

In the method shown in FIG. 13, more specifically, the nuclei of platinum are deposited by inserting the portion L1 of the substrate 20 into a shielding plate 90 having a hole for inserting the portion L1 of the substrate 20 thereinto and by fixing the substrate 20 in the ion coater 80 with its bottom portion being directed toward the negative electrode 83. According to this method, the platinum nuclei can be deposited all over the portion L1 of the substrate 20 without turning the substrate 20. If the bottom portion of the substrate 20 is coated with a shielding cover 91 made of rubber or the like, as shown in FIG. 14, the platinum nuclei can be deposited exclusively on the outer wall of the portion L1 of the substrate 20 excepting the bottom portion.

This application is based on Japanese Patent application JP 2002-322627, filed Nov. 6, 2002, the entire content of which is hereby incorporated by reference, the same as if set forth at length.

What is claimed is:

1. A process for manufacturing a gas sensor including a detecting element having an electrode containing a precious metal formed on a surface of a solid electrolyte, comprising:
    a first step of applying a nuclei of a precious metal on a surface of the solid electrolyte, the precious metal having a catalyzing action on a gas to be measured; and
    a second step of growing the nuclei,
    wherein the first step comprises physical vapor deposition and said second step comprises electroless plating.

2. The gas sensor manufacturing process according to claim 1, wherein said physical vapor deposition comprises sputtering.

3. The gas sensor manufacturing process according to claim 2, wherein at the first step, a glow discharge is conducted to ionize a residual gas so that the ionized residual gas collide against a target of precious metal foil to sputter atoms or molecules of precious metal on a surface of the solid electrolyte thereby to apply a nuclei of the precious metal atoms or molecules.

4. The gas sensor manufacturing process according to claim 3, wherein the precious metal is platinum.

5. The gas sensor manufacturing process according to claim 3, wherein at the first step, at least one of shielding plate and a shielding cover is arranged at a portion other than that to form an electrode.

6. The gas sensor manufacturing process according to claim 1, wherein at the second step, an aqueous solution of complex salt of platinum is used as an electrolessly plating liquid.

7. The gas sensor manufacturing process according to claim 6, wherein at the second step, a portion other than that, to which the nuclei of the precious metal have been applied at the first step, is electrolessly plated with a reducer having such a reducing power that the precious metal does not deposit.

8. The gas sensor manufacturing process according to claim 7, wherein an aqueous solution of platinic ammine or an aqueous solution of platinous ammine is used as the aqueous solution of complex salt of platinum, and hydrazine is used as the reducer.

9. The gas sensor manufacturing process according to claim 1, wherein at the second step, the electroless plating is conducted by leaving a substrate, to which the nuclei of the precious metal have been applied at the first step, to stand while being rocked in an electrolessly plating liquid.

10. The gas sensor manufacturing process according to claim 1, wherein the solid electrolyte is formed into a cylindrical shape having one end closed.

\* \* \* \* \*